United States Patent
Demergasso Semenzato et al.

(10) Patent No.: US 10,760,099 B2
(45) Date of Patent: Sep. 1, 2020

(54) METHOD FOR PRODUCING ARSENIC SULPHIDE NANOSTRUCTURES FROM FUSIBACTER ASCOTENCE AND PRODUCED NANOSTRUCTURES

(71) Applicant: UNIVERSIDAD CATÓLICA DEL NORTE, Antofagasta (CL)

(72) Inventors: Cecilia Demergasso Semenzato, Antofagasta (CL); Lorena Escudero González, Antofagasta (CL); Antonio E. Serrano, Antofagasta (CL)

(73) Assignee: UNIVERSIDAD CATÓLICA DEL NORTE, Antofagasta (CL)

( * ) Notice: Subject to any disclaimer, the term of this patent is extended or adjusted under 35 U.S.C. 154(b) by 0 days.

(21) Appl. No.: 16/061,918

(22) PCT Filed: Dec. 12, 2016

(86) PCT No.: PCT/CL2016/050066
§ 371 (c)(1),
(2) Date: Jun. 13, 2018

(87) PCT Pub. No.: WO2017/100959
PCT Pub. Date: Jun. 22, 2017

(65) Prior Publication Data
US 2018/0371500 A1   Dec. 27, 2018

(30) Foreign Application Priority Data
Dec. 14, 2015   (CL) .................................. 3614-2015

(51) Int. Cl.
| | | |
|---|---|---|
| *C12P 3/00* | (2006.01) | |
| *C01G 28/00* | (2006.01) | |
| *C12N 1/20* | (2006.01) | |
| *C12R 1/01* | (2006.01) | |
| *B82Y 40/00* | (2011.01) | |

(52) U.S. Cl.
CPC .............. *C12P 3/00* (2013.01); *C01G 28/008* (2013.01); *C12N 1/20* (2013.01); *C12R 1/01* (2013.01); *B82Y 40/00* (2013.01); *C01P 2002/72* (2013.01); *C01P 2002/82* (2013.01); *C01P 2002/84* (2013.01); *C01P 2002/85* (2013.01); *C01P 2004/04* (2013.01); *C01P 2004/16* (2013.01); *C01P 2004/51* (2013.01); *C01P 2004/61* (2013.01)

(58) Field of Classification Search
None
See application file for complete search history.

(56) References Cited

U.S. PATENT DOCUMENTS

| | | | |
|---|---|---|---|
| 8,012,727 B2 | 9/2011 | Hur et al. | |
| 8,465,721 B2 | 6/2013 | Edwards et al. | |
| 2009/0155876 A1* | 6/2009 | Hur ........................... | C12P 3/00 435/168 |
| 2014/0239249 A1 | 8/2014 | McFarlane et al. | |
| 2014/0272183 A1* | 9/2014 | Cooper ................ | B01D 71/022 427/532 |

OTHER PUBLICATIONS

Newman, D. et al. "Precipitation of Arsenic Trisulfide by Desulfotomaculum auripigmentum", Applied and Environmental Microbiology, May 1997, p. 2022-2028, vol. 63, No. 4 (7 pages).
"Fusibacter Ascotence" American Type Culture Collection, 2013, p. 1-2 (2 pages).
Thiruvengadathan et al. "Synergetic Effect of Ultrasound and Sodium Dodecyl Sulphate in the Formation of CdS Nanostructures in Aqueous Solution", Ultrasonic Sonochemistry, Mar. 2007, p. 398-404, vol. 14, No. 3 (7 pages).
International Search Report for related International Application No. PCT/CL2016/50066, dated Apr. 13, 2017; 3 pages; English translation provided.

* cited by examiner

*Primary Examiner* — Christian L Fronda
(74) *Attorney, Agent, or Firm* — Procopio, Cory, Hargreaves & Savitch LLP

(57) ABSTRACT

The present invention relates to the field of nanotechnology, more specifically to the manufacture or treatment of nanostructures, and in particular provides arsenic sulfide nanostructures, as well as a process for obtaining nanostructures of arsenic sulfide.

The present invention provides a process for obtaining arsenic sulfide (As—S) nanostructures from a microorganism, which comprises the steps of culturing under appropriate conditions the strain *Fusibacter ascotence* in the presence of a source of sulfur and a source of arsenic; and recovering arsenic sulfide nanostructures (As—S) from the precipitate obtained from said culture.

The present invention provides, also, a nanostructure of arsenic sulfide which is a nanowire having a monoclinic crystal structure. The present invention further provides a nanostructure of arsenic sulfide, which is a nanoparticle with a monoclinic crystal structure.

10 Claims, 6 Drawing Sheets

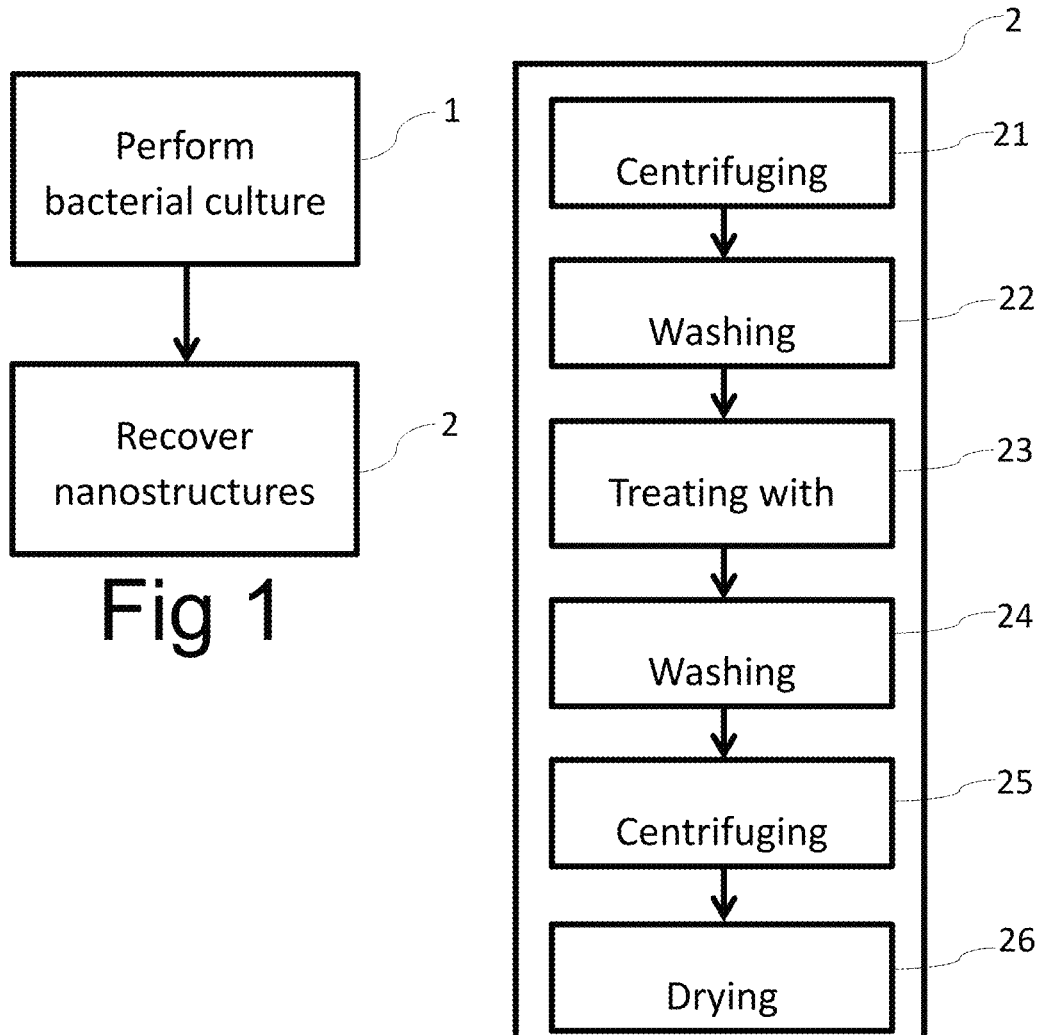

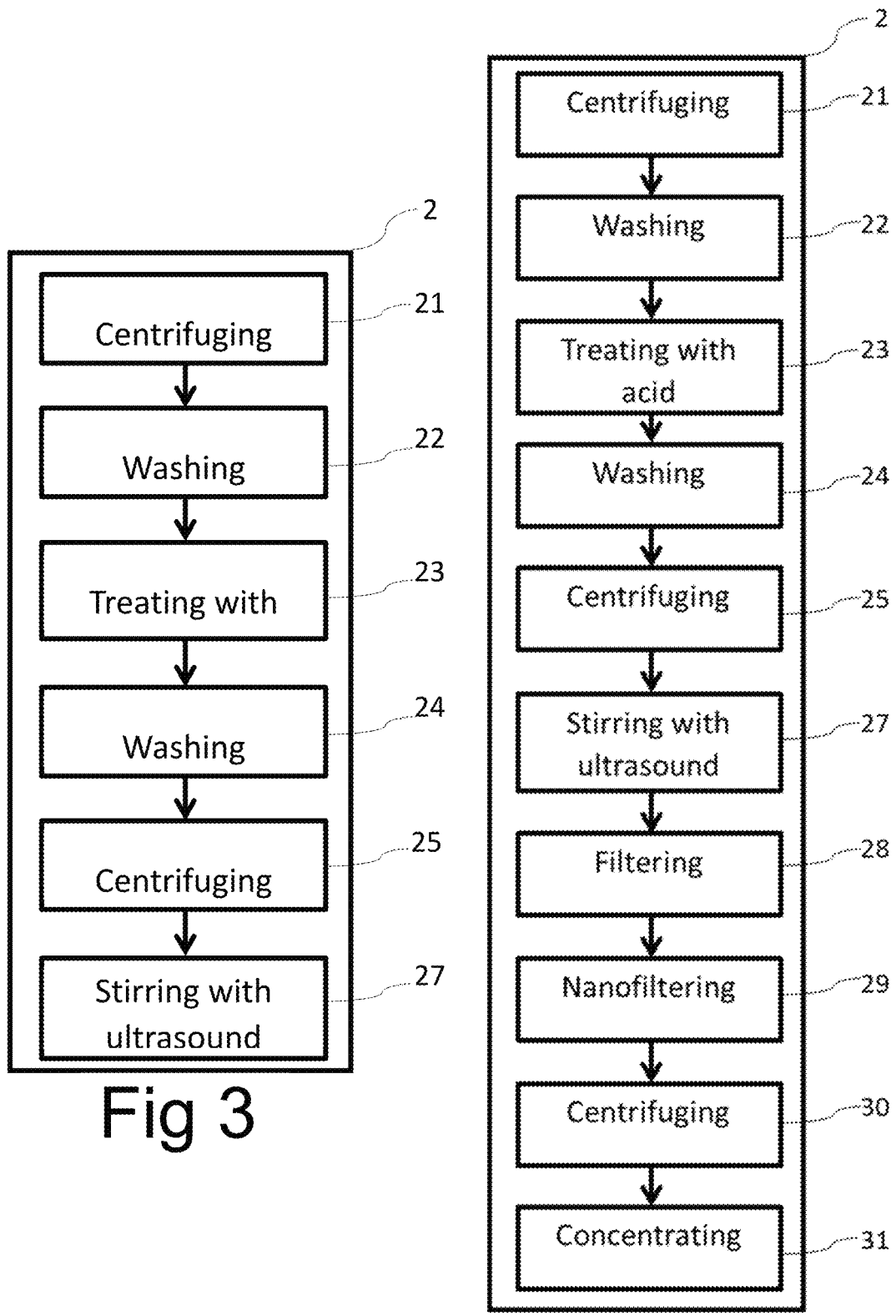

METHOD FOR PRODUCING ARSENIC SULPHIDE NANOSTRUCTURES FROM FUSIBACTER ASCOTENCE AND PRODUCED NANOSTRUCTURES

CROSS-REFERENCE TO RELATED APPLICATIONS

This application is a U.S. National Stage entry of PCT Application No: PCT/CL2016/050066 filed Dec. 12, 2016, which claims priority to Chilean Patent Application No. 3614-2015, filed Dec. 14, 2015, the contents of which are incorporated herein by reference.

TECHNICAL FIELD

The present invention relates to the field of nanotechnology, more specifically to the manufacture or treatment of nanostructures, and in particular provides arsenic sulfide nanostructures, as well as a process for obtaining nanostructures of arsenic sulfide.

BACKGROUND OF THE INVENTION

Within the field of nanotechnology, interest has arisen in obtaining nanostructures through the use of microorganisms. In general, it is recognized within the prior art that methods using microorganisms are more efficient than chemical or physical methods in terms of cost and environmental impact.

In the state of the art, processes have been reported using bacteria to obtain nanostructures of arsenic sulfide (As—S). For example, patent application US 2014/239,249 discloses a method of manufacturing As—S nanofibers using the bacterium *Shewanella* sp. ANA-3. On the other hand, U.S. Pat. No. 8,012,727 describes a method for making nanotubes of $As_2S_3$ that possess photoconductivity, using the bacterium *Shewanella* sp. HN-41, and to a lesser extent As—S in the form of tubes.

A method of biogenic manufacture of nanoparticles and quantum dots is also disclosed in U.S. Pat. No. 8,465,721. In this case, the nanoparticles obtained are a combination of an element of groups 15 or 16 (such as Sulfur or Arsenic) and one or more metals of groups 11, 12, 13 or 14. To recover the nanoparticles or quantum dots from the culture medium, the document mentions the possibility of acidifying the medium to induce a cellular flocculation and then centrifuging.

Prior art documents, however, do not mention the possibility of using other strains for the biogenic production of As—S nanostructures, nor do they mention the possibility of extracting both nanowires and nanoparticles from, essentially, the same process.

SUMMARY OF THE INVENTION

The present invention provides a process for obtaining arsenic sulfide (As—S) nanostructures from a microorganism which comprises the steps of culturing under appropriate conditions a bacterium of the phylum Firmicutes in the presence of a source of sulfur and a source of arsenic and recover nanostructures of arsenic sulfide (As—S) from the precipitate that is obtained from said culture.

In a preferred embodiment of the invention, said phylum Firmicutes strain is *Fusibacter ascotence*, deposited within the American Type Culture Collection under accession number ATCC BAA-2418.

In another preferred embodiment, the source of sulfur of the process is selected from the group consisting of an organic sulfur source and an inorganic sulfur source. In a more preferred embodiment, that said source of organic sulfur is selected from the group consisting of cysteine, yeast extract, as well as combinations thereof, and the inorganic sulfur source is selected from the group consisting of sodium sulfate, sodium thiosulfate, as well as combinations thereof.

In a preferred embodiment, the source of arsenic of the process is selected from the group consisting of arsenates, arsenic oxides, and combinations thereof.

In another preferred embodiment of the invention, that said appropriate culture conditions of *Fusibacter ascotence* are anaerobic conditions, in Newman culture medium, at a pH between pH 6 and 8, for more than 5 days and at a temperature between 20° C. and 37° C. In a more preferred embodiment, the culture duration is between 5 and 10 days.

In a preferred embodiment, the recovery of nanostructures of the process comprises the step of centrifuging the precipitate. In a more preferred embodiment, after the step of centrifuging the precipitate, the following steps are performed: washing the product obtained from the centrifugation; performing an acid treatment of said washed product; washing the product of the acid treatment; and centrifuging the product after the second washing. In an even more preferred embodiment, the acid treatment is carried out with hydrochloric acid.

In another more preferred embodiment, in order to obtain nanostructures in the form of nanowires, said process comprises the further step of drying the product obtained after the centrifuging step. In an even more preferred embodiment, the drying is carried out at a temperature higher than 50° C. and for a time greater than 18 hours.

In another more preferred embodiment, in order to obtain nanostructures in the form of nanoparticles, said process comprises the further step of stirring the product obtained after the centrifuging step by ultrasound. In an even more preferred embodiment, said ultrasonic stirring is performed in the presence of an anionic detergent. In an even more preferred embodiment, said anionic detergent is sodium dodecyl sulfate. In yet another preferred embodiment, after the ultrasound stirring step, the process comprises the steps of filtering the product of said ultrasound stirring; performing a nanofiltration of the product obtained after filtration; centrifuging the product obtained after the nanofiltration; and concentrating the product obtained after centrifugation.

The present invention further provides an arsenic sulfide nanostructure which is a nanowire having monoclinic crystalline structure. In a preferred embodiment, the thickness of said nanowire follows a distribution whose average is 171 nm and whose standard deviation is 85.3 nm. In another preferred embodiment, said nanowire has a maximum absorption at a wavelength of 430 nm and a prohibited bandwidth of 2.24 eV.

The present invention further provides an arsenic sulfide nanostructure in the form of a nanoparticle having monoclinic crystalline structure. In a preferred embodiment, the diameter of said nanoparticle follows a distribution whose average is 143 nm and whose standard deviation is 25.85 nm.

BRIEF DESCRIPTION OF THE DRAWINGS

FIG. 1 is a flowchart of the process for obtaining nanostructures which is subject matter of the present invention.

FIG. 2 is a flowchart of a first embodiment of the sub-process for recovery of nanostructures which is subject matter of the present invention.

FIG. 3 is a flowchart of a second embodiment of the sub-process for recovery of nanostructures which is subject matter of the present invention.

FIG. 4 is a flowchart of a third embodiment of the sub-process for recovery of nanostructures which is subject matter of the present invention.

DETAILED DESCRIPTION OF THE INVENTION

Figure 5:
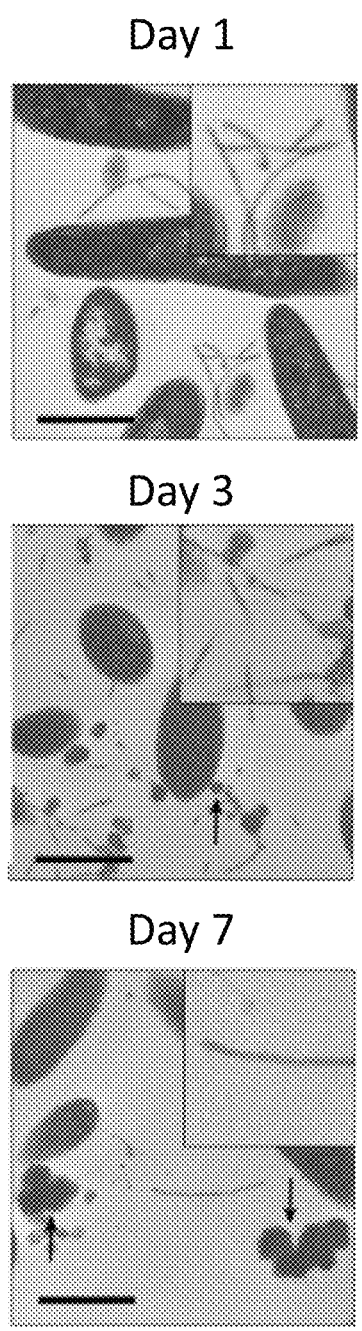
FIG. 5 is a sequence of photographs indicating the dependency of the obtention of nanostructures as a function of the duration of the culture.

The process for obtaining nanostructures of arsenic sulfide (As—S) which is subject matter of the present invention will now be described in detail.

The term "nanostructures" should be understood as those structures having at least one of their dimensions (length, width or depth) in the range of 1 nm to 500 nm. The term "nanowires" should be understood as those structures, either solid or hollow, in elongated form, similar to a wire or thread, not necessarily straight, and whose average thickness is in the range of 1 nm to 500 nm. The term "nanoparticles" should be understood as those structures in the form of particles, not necessarily spherical, and whose equivalent diameter is in the range between 1 nm and 500 nm. It will be understood as the equivalent diameter of a nanoparticle the diameter of a sphere that occupies the same volume as the nanoparticle.

In relation with FIG. 1, the process for obtaining arsenic sulfide (As—S) nanostructures from a microorganism which is the subject matter of the present invention comprises two main steps: first, a culture (1) of the *Fusibacter ascotence* strain is performed under appropriate conditions and in the presence of at least one source of sulfur and at least one source of arsenic until a precipitate is obtained; secondly, recovery (2) of the As—S nanostructures is performed from said precipitate.

The appropriate conditions for the cultivation (1) of *Fusibacter ascotence* will be understood as those that allow reproduction and proliferation of said strain. With regard to the culture temperature, it will be understood that a temperature in the range of 20° C. to 37° C. constitutes an appropriate condition, without limiting the scope of the present invention. With regard to the pH of the culture, it will be understood that a pH of between 6 and 8 is an appropriate condition, without limiting the scope of the present invention. It will be further understood, and without limiting the scope of the present invention, that an appropriate condition is cultivation under anaerobic conditions.

Regarding the culture medium, while any suitable culture medium for this strain may be used to carry out the present invention, in a preferred embodiment the culture of *Fusibacter ascotence* is carried out in a Newman culture medium (Newman et al., Applied and Environmental Microbiology, 1997, Vol. 63, No. 5, pp 2022-2028). Further, in relation to the duration of cultivation, it will be understood that an appropriate condition is one in which the bacterium is grown for a time greater than 3 days, more particularly, without limiting the scope of the present invention, greater than 5 days, and more particularly, without limiting the scope of the present invention, between 5 and 10 days.

The sulfur source, at least one, mentioned in the step of performing a culture (1) of *Fusibacter ascotence* can be an organic or inorganic source, as well as combinations between both types of sulfur source. Within the group of organic sulfur sources, for example, and without limiting the scope of the present invention, cysteine or yeast extract, as well as combinations thereof, may be used. Within the group of inorganic sulfur sources, for example and without limiting the scope of the protection, sodium sulfate or sodium thiosulfate, as well as combinations thereof, may be used.

The at least one source of arsenic mentioned in the step of performing a *Fusibacter ascotence* culture (1) can be selected, without limiting the scope of the present invention, from the group consisting of arsenic or arsenic oxides, as well as combinations thereof.

With respect to the step of recovering (2) the nanostructures from the precipitate obtained in the previous step, any form of recovery is suitable for carrying out the present invention, without this limiting the scope of the protection being sought. The way in which the nanostructures are recovered will depend on the specific applications of the same. In particular, any method of recovery which enables the removal of water and organic matter from the precipitate as well as dispersion of the As—S nanostructures, if desired, is within the scope of the present invention.

In the following, sub-processes will be described in detail to allow the recovery of As—S nanostructures from the precipitate obtained after the culture. As mentioned above, these sub-processes are intended to be illustrative but should not be considered under any circumstances to limit the scope of the present invention.

With respect to FIGS. 2, 3 and 4, the step of recovering (2) the nanostructures from the precipitate comprises the step of centrifuging (21) the precipitate. The specific sub-process will depend on the shape of the nanostructures to be obtained.

In a preferred embodiment of the present invention, after the centrifuging step (21) of the precipitate obtained from the culture (1), a first washing (22) of the obtained product (21) is performed. This first wash (22) can be carried out, for example and without limiting the scope of the present invention, with distilled water and can be carried out by resuspending the product obtained from the centrifugation in approximately 10 volumes of distilled water. However, other solvents may be used to perform such wash, and other ratios may be used between the volume of the precipitate and the volume of the solvent. In another preferred embodiment, and without limiting the scope of the present invention, said suspension can be agitated and then the obtained product can be centrifuged (21). The steps of centrifuging (21) and washing (22) the precipitate can be performed iteratively without limiting the scope of the present invention.

After washing (22), the acid (23) treatment of the precipitate is carried out. The aim of this treatment with acid (23) is to eliminate in the precipitate residues of free biomass, molecules or organic compounds which are not classified as minerals. A person skilled in the art will note, however, that such acid treatment (23) may be carried out before washing (22) or centrifuging (21) steps. In an exemplary embodiment, the acid treatment (23) is performed by adding approximately 10 volumes of hydrochloric acid (5N HCl) to the product obtained after washing (22) step and then stirring said mixture. A person skilled in the art will appreciate, however, that other acids and other concentrations may be used to obtain the result of removing the above-described debris without limiting the scope of the present invention.

After the acid treatment (23), a second washing (24) step of the product obtained from said treatment with acid (23) is carried out. The same detailed options for the first wash (22) are applicable for this second wash (24). After this second washing (24) a second centrifuging step is performed (25). In particular, and without limiting the scope of the present invention, it is possible to perform this second washing (24) and this second centrifugation (25) in an iterative manner.

Various embodiments of the invention may be obtained from this point. With respect to FIG. 2, in order to obtain As—S nanostructures in a substantially nanowire form, after said second centrifuging step (25), the product obtained from said second centrifugation (25) is dried. This drying step (26) can be made at a suitable temperature to remove the remaining water in the product obtained after centrifugation, and for a suitable time to carry out said removal. For example, and without limiting the scope of the present invention, this drying step (26) can be carried out at a temperature above 50° C. On the other hand, and without limiting the scope of the present invention, said drying step (26) can be carried out for a time greater than 12 hours.

On the other hand, with respect to FIGS. 3 and 4, to obtain As—S nanostructures in a form substantially as nanoparticles, after the second spin (25) an ultrasound agitation (27) is performed. Said stirring (27) can be carried out, without limiting the scope of the present invention, in the presence of an anionic detergent. The presence of said anionic detergent aims to avoid the aggregation of the nanostructures, which facilitates its dispersion at the moment of the ultrasonic agitation (27). In a preferred embodiment, without limiting the scope of the present invention, the anionic detergent used is Sodium Dodecylsulfate (SDS), however, a person skilled in the art will appreciate that any anionic detergent which enables the above detailed result to be obtained is suitable for carrying out the present invention.

Referring to FIG. 4, after ultrasonic agitation (27), it is possible to perform additional steps to purify and concentrate the nanoparticles obtained. First, a filtration step (28) of the solution obtained after the ultrasound stirring (27) is carried out. This filtration (28) can be made, for example and without limiting the scope of the present invention, in a syringe-type filter. The size of the filter used for such filtration (28) does not limit the scope of the present invention, provided that it is a size suitable to retain one part of the solution and allow the other part to pass. After such filtration (28), it is possible, without limiting the scope of the present invention, to perform a nanofiltration step (29) of the part of the solution which passed the filter used in the first filtration (28). As in the previous case, the manner in which this nanofiltration step (29) is performed does not limit the scope of the present invention. As in the case of filtration (28), any filter size suitable for nanofiltration can be used. After said nanofiltration (29), it is possible to perform a third centrifugation step (30) of the part of the solution which passed the nanofiltration (29), to then perform a concentration step (31) of the product obtained after said third centrifugation (30). Said concentration (31) can be performed by any method which allows to reduce the volume of the product obtained after the third centrifugation (30).

With the process detailed above it is possible to obtain As—S nanostructures, both in the form of nanowires and nanoparticles, from a microorganism, specifically *Fusibacter ascotence*. Specific examples of embodiment of the present invention will now be described. It should be understood that these examples seek to better illustrate some technical aspects of the invention, but do not seek to limit the scope thereof.

EXAMPLES

Example 1: Culture of *Fusibacter ascotence*

An initial inoculum of $1\times10^6$ cells/mL of the *Fusibacter ascotence* strain deposited with the American Type Culture Collection with ATCC accession number BAA-2418 was used. The cells are bacilli straight or slightly curved, sometimes paired, mobile and gram positive.

The inoculums of the strain *Fusibacter ascotence* were cultured in serum-type bottles capped with butyl rubber plugs, in 100 mL of modified Newman liquid medium. Sodium thiosulfate (10 mM), sodium sulfate (10 mM) and mineral sulfur (1%) were included as inorganic sulfur sources. Yeast extract (0.2%) and cysteine (1 mM) were also included as sources of organic sulfur. Sodium arsenate (2 mM) was included as the source of arsenic. The bottles were hermetically sealed. A nitrogen atmosphere was blown for 5 minutes to displace the oxygen and obtain an anaerobic culture atmosphere. Cultures were carried out in up to 10 days in the dark under anaerobic conditions, with a temperature between 20° C. and 37° C. and a pH between 6 and 8.

Example 2: Obtention of Nanostructures in Dependency of the Culture Period

FIG. 5 shows photographs obtained by TEM (Transmission Electron Microscopy) of the bacterial cultures. The bars represent a size of 600 nm. It is observed the appearance of aggregates of nanostructures from the third day of culture. Aggregate size increases over time. In the inserts, on the other hand, the appearance of nanometric fibers is observed from the first day of culture.

Example 3: Recovery of Nanostructures

After 10 days of cultivation, a yellow precipitate is observed in the bottom of the bottles. The whole liquid was collected in 50 mL conical tubes and then centrifuged at 4,000 g for 5 minutes. The resulting pellet, about 5 mL, was resuspended in 10 volumes of distilled water, and then vortexed. After this washing step, centrifugation was performed at 4,000 g for 5 minutes. The washing and centrifugation steps were performed iteratively until 3 washes were completed.

After the washing and centrifugation steps a treatment with hydrochloric acid was carried out. For this purpose, 10 volumes of 5N HCl were added to the precipitate in a conical tube. It was shaken vigorously for 3 minutes and incubated on a rotary shaker for 18 hours. After the acid treatment, 3 washes of up to 10 times the initial volume were applied with distilled water with subsequent centrifugation for 5 minutes at 4,000 g.

Example 4: Obtention of Nanocables

After centrifugation, a concentrated solution of precipitate is obtained. In this solution, nanowires can be observed by optical microscopy for wires larger than 1 micrometer, or by electron microscopy for wires with a width of 20 nm. The concentrated solution is transferred to glass vials and dried in an oven at a temperature of 50° C. and for a period of 12 hours.

Example 5: Obtention of Nanoparticles

The pellet obtained after the last centrifugation step was resuspended in 10 volumes of 0.1% sodium dodecylsulfate and shaken by sonication with rod for 5 minutes on ice, using a glass flask. After ultrasonic agitation, a microfiltration of the aqueous solution was performed using a syringe-type filter with a 0.22 μm opening. A volume of less than 20 mL of the filtered solution was processed into a second nanofiltration step using a 0.025 μm filter installed in a vacuum pump and Kitasato-type flask system. The volume obtained after the nanofiltration was centrifuged at 16,000 g for 30 minutes at room temperature and then a vacuum concentrator was used to reduce the volume.

Example 6: Characterization of Nanostructures

Figure 6:
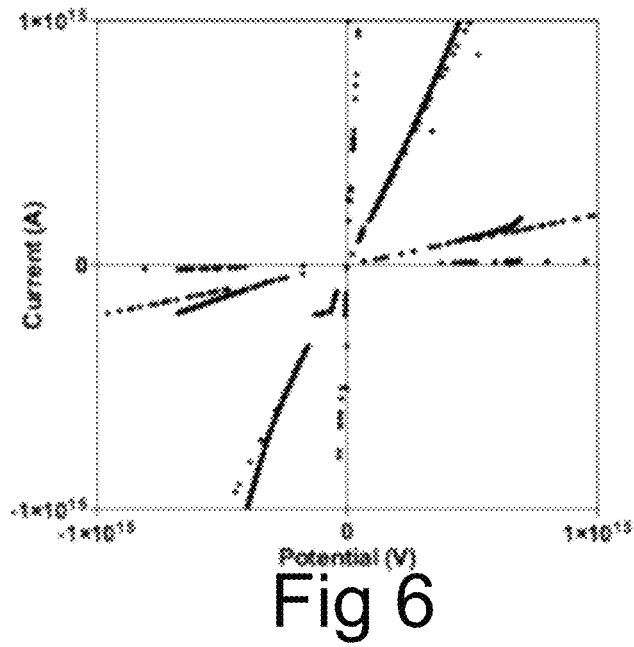
FIG. 6 is a graph of electrical current versus potential of tablets made from the nanowires that are subject matter of the present invention.
Figure 7:
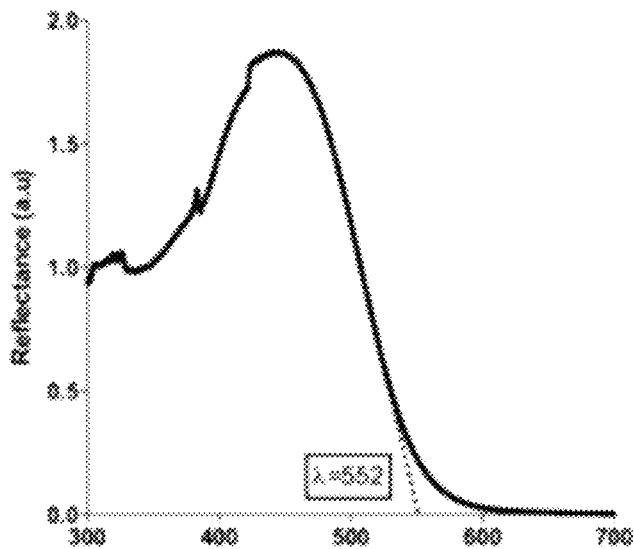
FIG. 7 is a UV-Vis spectrum of tablets manufactured from the nanowires which are subject matter of the present invention.

Transmission electron microscopy (TEM), UV-Vis spectroscopy, X-ray diffraction (XRD), Raman spectroscopy and atomic force microscopy (AFM) were used for the analysis and characterization of the obtained nanostructures. FIG. 6 shows an electrical current versus potential (I-V) curve of compacted tablets from the obtained nanowires. It is noted that said tablets possess semiconductor properties. FIG. 7 shows an absorption spectrum of said tablets, where it is observed that the maximum absorbance is at 450 nm, coinciding in large part with the solar emission maximum of approximately 475 nm. By calculating the wavelength that intersects the reflectance equal to zero, a prohibited bandwidth of these nanostructures of 2.24 eV is obtained. The previous results show that the nanostructures obtained can be used in photovoltaic cells.

Figure 11:
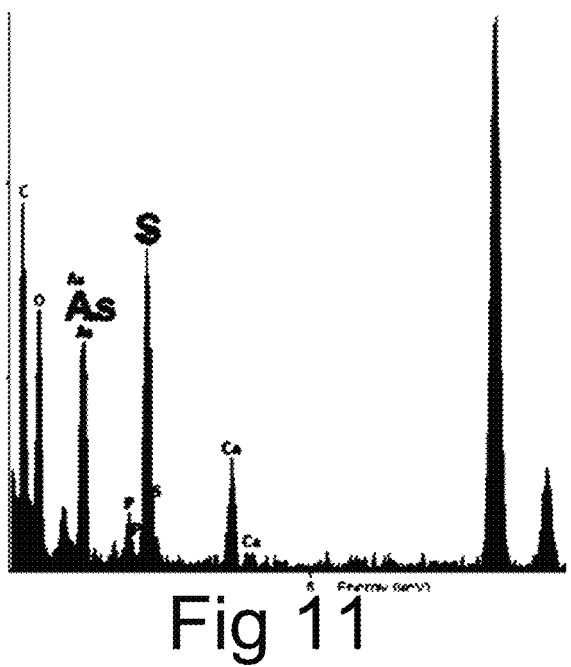
FIG. 11 is an EDX spectrum of the nanoparticles shown in FIG. 9.
Figure 12:
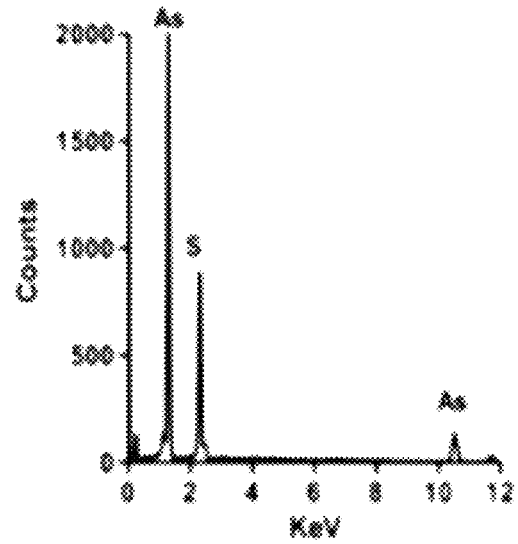
FIG. 12 is an EDX spectrum of the nanowires shown in FIG. 10.

Analysis of the XRD spectra of the obtained nanostructures shows that the nanostructures correspond to a crystalline species known as Rejalgar ($As_4S_4$), which has monoclinic crystal structure. The EDX spectra, shown in FIG. 11 for the case of the nanoparticles and in FIG. 12 for the case of nanowires, show that the As/S molar ratio is 1.05, which is shown in agreement with the stoichiometry of the Rejalgar structure.

Figure 8:
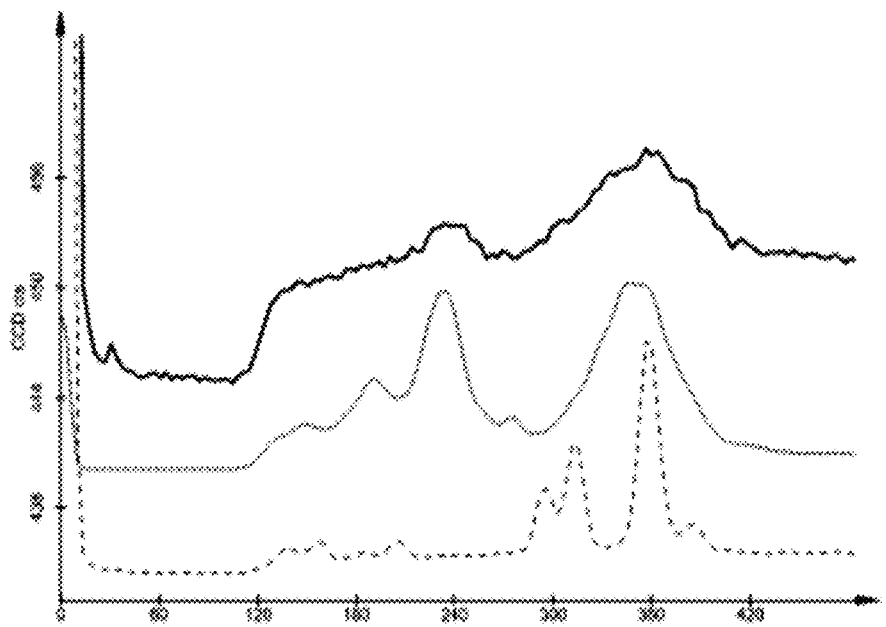
FIG. 8 is a Raman spectrum of nanostructures obtained according to the process that is subject matter of the present invention.

The Raman spectrum of nanostructures is shown in FIG. 8 as a continuous line. As a reference, the standard spectrum of Rejalgar is included in dotted line, which corresponds well with the spectrum of the nanostructures obtained. Also included is the standard spectrum of orpiment in a dashed line, which does not correspond to the spectrum of the nanostructures. This result confirms the conclusion that the obtained nanostructures correspond to the crystalline Rejalgar species.

Figure 9:
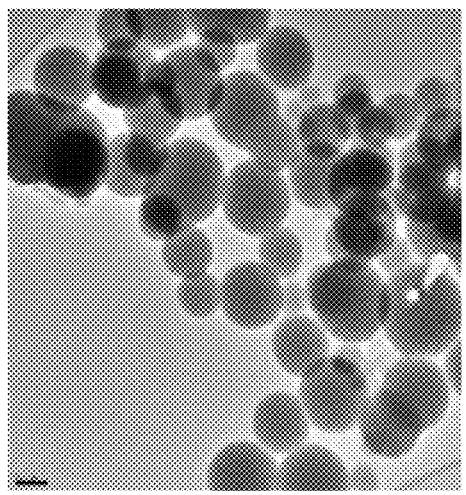
FIG. 9 is a TEM image of nanoparticles obtained by the process which is subject matter of the present invention.
Figure 13:
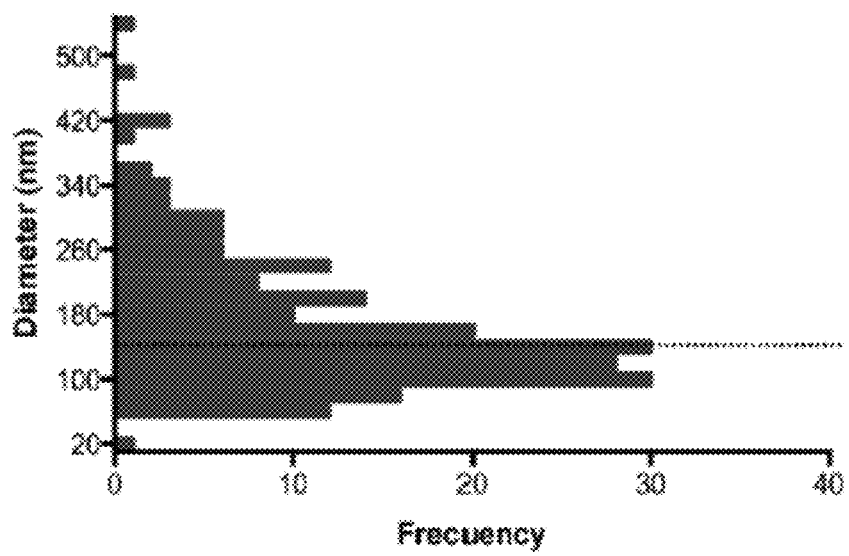
FIG. 13 is a frequency histogram of the diameter of the nanoparticles obtained by the process that is subject matter of the present invention.

FIG. 9 shows an image taken by TEM of the nanoparticles obtained. In this, the bar indicates a length of 220 nm. A distribution histogram of equivalent diameters is shown in FIG. 13. From these it is observed that the average diameter of these nanoparticles is 143 nm with a standard deviation of 25.85 nm.

Figure 10:
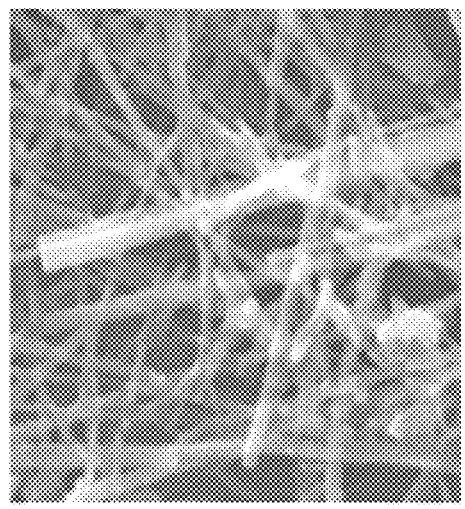
FIG. 10 is a TEM image of nanowires obtained by the process which is subject matter of the present invention.
Figure 14:
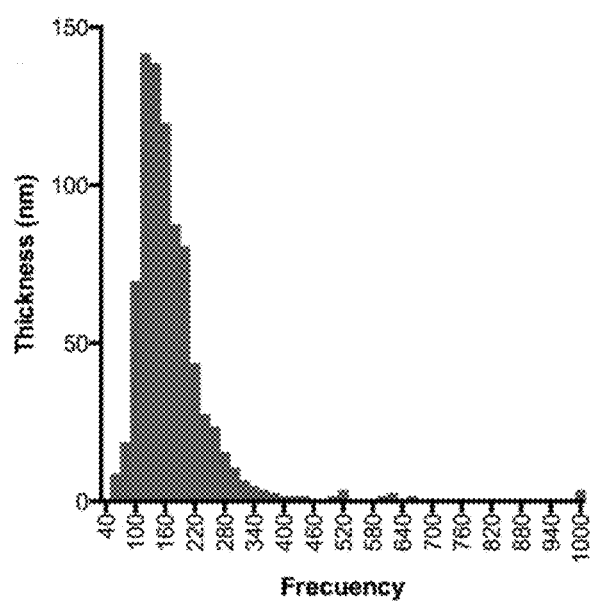
FIG. 14 is a frequency histogram of the thickness of the nanowires obtained by the process that is subject matter of the present invention.

FIG. 10, on the other hand, shows an image taken by TEM of the nanowires obtained. It is observed that the wires have both variable width and length. A histogram of frequencies of the thickness of the nanowires is shown in FIG. 14. The tests performed indicate that the average thickness of these nanowires is 171 nm, with a standard deviation of 85.3 nm. The length, as already mentioned, is variable, reaching in many cases lengths greater than 10 μm.

The invention claimed is:

1. A process for obtaining arsenic sulfide (As—S) nanostructures from a microorganism, comprising the steps of:
   culturing under appropriate conditions the strain Fusibacter ascotence, deposited within the American Type Culture Collection under accession number ATCC BAA-2418 in the presence of a source of sulfur and a source of arsenic; and
   recovering nanostructures of arsenic sulfide (As—S) from the precipitate obtained from said culture.

2. The process of claim 1, wherein said sulfur source is selected from the group consisting of an organic sulfur source and an inorganic sulfur source.

3. The process of claim 2, wherein said source of organic sulfur is selected from the group consisting of cysteine, yeast extract and combinations thereof; and the source of inorganic sulfur is selected from the group consisting of sodium sulfate, sodium thiosulfate and combinations thereof.

4. The process of claim 1, wherein said source of arsenic is selected from the group consisting of arsenates, arsenic oxides and combinations thereof.

5. The process of claim 1, wherein said appropriate culture conditions of Fusibacter ascotence ATCC BAA-2418 are anaerobic conditions in Newman culture medium at pH 6 to pH 8 for 5 to 10 days and at a temperature between 20° C. and 37° C.

6. The process of claim 1, wherein the recovery of nanostructures comprises the further steps of:
   centrifuging the precipitate;
   washing the product obtained from the centrifuging step;
   treating said washed product with acid;
   performing a second washing of the acid treated product;
   performing a second centrifugation of the product after the second washing.

7. The process of claim 6, wherein the acid treatment is performed with hydrochloric acid.

8. The process of claim 6, wherein in order to obtain nanostructures in the form of nanowires, said process comprises the further step of drying the product obtained after the second centrifugation at a temperature greater than 50° C. and for a time greater than 12 hours.

9. The process of claim 6, wherein in order to obtain nanostructures in the form of nanoparticles, said process comprises the further step of ultrasonic stirring the product obtained after the second centrifugation in the presence of an anionic detergent.

10. The process of claim 9, wherein after the ultrasound agitation step further comprises the steps of:

filtering the product obtained after agitation by ultrasound;
performing a nanofiltration of the product obtained after filtration;
centrifuging the product obtained after the nanofiltration; and
concentrating the product obtained after centrifugation.

* * * * *